United States Patent [19]
Cuthbert et al.

[11] Patent Number: 5,668,171
[45] Date of Patent: Sep. 16, 1997

[54] HALOGENATED MEVALONATE COMPOSITIONS AND USES THEREOF IN RAS-DEPENDENT CELL GROWTH

[75] Inventors: Jennifer A. Cuthbert; Peter E. Lipsky, both of Dallas, Tex.

[73] Assignee: Board of Regents, The University of Texas System, Austin, Tex.

[21] Appl. No.: 148,148

[22] Filed: Nov. 8, 1993

[51] Int. Cl.$^6$ .................................................. A61K 31/35
[52] U.S. Cl. ............................................................. 514/460
[58] Field of Search .............................................. 514/460

[56] References Cited

U.S. PATENT DOCUMENTS 5,244,916  9/1993  Bokoch .................................. 514/460

OTHER PUBLICATIONS

Bos, J.L., The ras gene family and human carcinogenesis, *Mutation Research*, 195: 255–271, 1988.

Cuthbert, J.A. and Lipsky, P.E., Selective supression of activated p21ras-dependent proliferation by fluoromevalonate, Abstract No. BZ 403, *Journal of Cellular Biochemistry*, 17(A), Suppl., p. 279, Jan. 1993.

Cuthbert, J.A. and Lipsky, P.E., Negative Regulation of Cell Proliferation by Mevalonate or One of the Mevalonate Phosphates, *J. Biol. Chem.*, 266: (27) 17966–17971, 1991.

Cuthbert, J.A. and Lipsky, P.E., Inhibition by 6-Fluoromevalonate Demonstrates That Mevalonate or One of the Mevalonte Phosphates is Necessary for Lymphoctye Proliferation, *J. Biol. Chem.*, 265: (30) 18568–18575, 1990.

Quistad, et al., Fluoromevalonate —an inhibitor of insect juvenile hormone biosynthesis, *Scientific Papers of the Institute of Organic and Physical Chemistry of Wroclaw Technical University*, No. 22, Conferences 7, 163–168, 1981.

Reardon, J.E. and Abeles, R.H., Inhibition of cholesterol biosynthesis by fluorinated mevalonate analogues, *Biochemistry*, 26: 4717–4722, 1987.

Conley and Van Echo, "Antineoplastic Drug Development," *The Chemotherapy Source Book*, Principles of Chemotherapy, Section One, Michael C. Perry, Ed., Williams & Wilkins, Baltimore, MD, Publishers, pp. 15–21, 1992.

Gibbs, Jackson B., "Ras C–Terminal Processing Enzymes–New Drug Targets?" *Cell*, 65:1–4, 1991.

Hagg et al., "Limonene–Induced Regression of Mammary Carcinomas," *Cancer Research*, 52:4021–4026, 1992.

Hara et al., "Identification of Ras Farnesyltransferase Inhibitors by Microbial Screening," *Proc. Natl. Acad. Sci. USA*, 90:2281–2285, 1993.

*Rodent Tumor Models in Experimental Cancer Therapy*, Robert F. Kallman, Ed., Pergamon Press, Elmsford, NY, Publishers, Table of Contents, pp. v–ix, 1987.

Kohl et al., "Protein Farnesyltransferase Inhibitors Block the Growth of ras–dependent Tumors in Nude Mice," *Proc. Natl. Acad. Sci.*, 91:9141–9145, 1994.

Miller et al., "Increased Radioresistance of EJras–Transformed Human Osteosarcoma Cells and Its Modulation by Lovastatin, an Inhibitor of p21$^{ras}$ Isoprenylation", *Int. J. Cancer*, 53:302–307, 1993.

Moyer and Fischer, "The Promise of Oncogene Inhibitors as Novel Antitumor Agents," *Cancer Chemotherapy*, Chapter 1, pp. 1–20, John A. Hickman and Thomas R. Tritton, Eds., Blackwell Scientific Publications, Publishers, Boston, MA, 1992.

Ruch et al., "Reversal of ras–Induced Inhibition of Gap––Junctional Intercellular Communication, Transformation, and Tumorigenesis by Lovastatin," *Molecular Carcinogenesis*, 7:50–59, 1993.

PCT Search Report mailed Aug. 11, 1994.

Leonard et al., "Inhibition of Isoprenoid Biosynthesis and the Post–translational Modification of pro–p21$^{ras}$," *The Journal of Biological Chemistry*, 265(9):5157–5160, 1990.

*Primary Examiner*—Jerome D. Goldberg
*Attorney, Agent, or Firm*—Denise L. Mayfield, Esq.

[57] ABSTRACT

Compositions that include as an active ingredient an effective concentration of a halogenated mevalonate preparation, particularly, Fmev (fluoromevalonate) are provided. The pharmacological activity of halogenated mevalonate for inhibiting ras-dependent cell growth, particularly ras-dependent tumor cell growth, is described. Methods for using preparations including a therapeutically effective concentration of Fmev for the inhibition of ras-dependent cell growth, as well as in the treatment and inhibition of ras-dependent tumors is also disclosed. The claimed compositions may be provided in liquid, salve, tablet, or capsule form, as well as other forms suitable for administration to an animal.

16 Claims, 11 Drawing Sheets

HALOGENATED MEVALONATE COMPOSITIONS AND USES THEREOF IN RAS-DEPENDENT CELL GROWTH

The United States Government owns rights in the present invention as research relating to the development of the invention was supported by PHS grant AI17653.

BACKGROUND OF THE INVENTION

1. Field of the Invention

The present invention relates generally to the field of transformed cells. More particularly, it concerns Ras-transformed cells and provides compositions and methods for selectively inhibiting the growth of cells with ras mutations.

2. Description of the Related Art

In normal cells, Ras, a plasma membrane-associated 21 kDa guanine nucleotide-binding protein, is involved in important cellular events on the molecular level, particularly signal transduction events associated with both normal and oncogenic cell growth and differentiation (Barbacid, 1987). In normal cells, Ras is activated following the stimulation of fibroblasts by growth factors (Lu and Campisi, 1992) the stimulation of hematopoietic cells by the cytokines interleukin-3 and granulocyte-macrophage colony-stimulating factor (Satoh et al., 1991), and the stimulation of T lymphocytes by the cytokine, interleukin-2 and antibodies to the T cell antigen receptor and the alternative activation molecule, CD2 (Downward et al., 1990; Graves et al., 1992). The exact function of activated Ras in normal cells has not been defined. However, its importance has been inferred from studies demonstrating that depletion of normal levels of Ras or neutralization of Ras activity interferes with cell growth.

The Ras protein has also been associated with oncogenic cell growth. For example, about 20% of all human tumors have been found to have a mutation that activates a cellular ras proto-oncogene (Barbacid, 1987); these mutations are particularly prevalent in common cancers such as adenocarcinomas of the colon (Fearon et al., 1990) and pancreas (Almaguera et al., 1988), as well as in non-small cell lung carcinoma (Mitsudomi, et al., 1991). Oncogenic forms of Ras are constitutively active, generally as the result of a point mutation that leads to the accumulation of GTP-bound Ras (Grand et al., 1991).

Membrane association of Ras is important for in vitro transforming activity and is, in normal cells, dependent on post-translational modification of the carboxy-terminus by sequential farnesylation, proteolysis and carboxymethylation (Willumsen et al., 1984; Hancock et al., 1989 cell). In addition, either a polybasic domain or palmitoylation is necessary for localization to the plasma membrane (Hancock et al., 1990). Of this step-wise series of post-translational modifications, initial farnesylation appears to be a requisite event for both membrane association and in vitro transformation by oncogenic Ras (Jackson, et al., 1990; Hancock et al., 1990). Interference with post-translational farnesylation of Ras prevents subsequent membrane localization (Willumsen et al., 1984; Jackson et al., 1990; Karo et al., 1992).

Recent studies have elucidated the biochemical processes that convert cytosolic Ras into its membrane-associated form. In the initial farnesylation step, cytosolic farnesyl-protein transferase utilizes farnesyl pyrophosphate to modify cysteine-186 in the carboxy-terminal sequence of cytosolic Ras. Inhibition of the synthesis of farnesyl pyrophosphate, by blocking the formation of the precursor mevalonate with lovastatin, prevents post-translational processing of Ras and subsequent membrane localization. Theoretically, therefore, lovastatin may be able to inhibit proliferation of Ras-transformed cells by blocking farnesylation, if the cell growth is Ras-dependent. However, other cellular effects of the inhibition of mevalonate synthesis by lovastatin interfere with its usefulness in determining the role of farnesylation of Ras and also limit its potential ability to inhibit the growth of Ras-transformed cells selectively.

Lovastatin inhibits the proliferation of all cells by preventing the synthesis of at least two essential products of mevalonate metabolism (FIG. 1). One of these products has been clearly shown to be cholesterol. The other product has only been defined indirectly and has not been identified. Thus, when the synthesis of mevalonate is blocked with lovastatin or related specific inhibitors of 3-hydroxy-3-methylglutaryl coenzyme A (HMG-CoA) reductase, cell proliferation is completely prevented. Neither trace quantities of mevalonate nor its end-product cholesterol is individually able to restore growth. However, when both are added together, proliferation is totally restored. These studies provide evidence that both cholesterol and non-sterol products derived from mevalonate are each required for normal cell growth. It should be noted that neither the number nor the identity of the non-sterol product(s) of mevalonate required for cellular proliferation has been defined. Furthermore, whether the role of the mevalonate product(s) in the proliferation of transformed cells is different than the role in non-transformed cells has not been clarified.

The most preferred forms of cancer therapy are designed to control the growth of malignant cells, while permitting proliferation and function of normal cells. However, many chemotherapeutic agents and cancer-directed pre- and post-surgery treatments destroy or otherwise severely compromise the non-cancerous population of cells in the patient. Although the rational behind such therapies is that any remaining non-oncogenic, healthy cells in the patient will repopulate and restore the patient to an improved immunological state, it is, of course, well-known that all current treatment methods for cancer are far from satisfactory and that improved therapeutic regimens are needed.

SUMMARY OF THE INVENTION

The present invention seeks to overcome these and other drawbacks inherent in the prior art by providing a halogenated mevalonate preparations, particularly mono and 6,6-di halogenated mevalonate analogues that may specifically inhibit the proliferation of transformed cells without affecting normal cell growth. The present invention thus provides advantageous methods for selectively inhibiting cancer cell growth, both in vitro and in vivo. Treatment methods employing halogenated mevalonate preparations provide a superior and attractive alternative to conventional clinical regimens for the treatment of cancer. Halogenated forms of mevalonate that may be employed in the described methods include 6-fluoromevalonate, 6,6-difluoromevalonate, 6-iodomevalonate, 6,6-diiodomevalonate, 6,bromomevalonate, 6,6-dibromomevalonate, 6-chloromevalonate, and 6,6-dichloromevalonate. The most preferred mevalonate preparations for the claimed methods are the 6-monohalogen substituted forms of mevalonate, such as 6-fluoromevalonate (Fmev).

The invention is partly embodied in the inventors' surprising finding that Fmev blocks the post-translational farnesylation of Ras. Surprisingly, the oncogenic potential of activated Ras is blocked. Moreover, and of an even more surprising nature, malignant cells that are transformed by activated Ras, are demonstrated to effect a reverse in the malignant cell phenotype. Thus, novel methods for treating as well as actually reversing tumors and tumor growth have been discovered and are disclosed herein.

The unique combination of alterations in mevalonate metabolism that occur in transformed cells may thus be advantageously employed to inhibit the progression of mevalonate responsive cancers in the patient. As about 20% of all human tumors are the result of a mutation that activates a cellular ras-proto-oncogene, the claimed therapies and methods will provide an attractive alternative to conventional chemotherapy treatments in a significant segment of the population.

Ras mutations are known to occur in many types of malignancies, for example, in cancers of the breast, urinary tract, stomach, colon, liver, lung, cervix, ovary, pancreas and gall bladder, and also in fibrosarcomas, rhabdomyosarcomas, teratocarcinomas and diseases such as AML, CML, ALL, Burkitt's lymphoma and Hodgkin's disease (Bos, 1988, incorporated herein by reference). The present invention is therefore widely applicable to the treatment of any and all cancers which include a ras gene mutation within the transformed cells.

The present inventors have observed that, surprisingly, the proliferation of transformed cells in vitro is inhibited by Fmev, whereas normal cell growth under the same culture conditions remains unaffected. This particular selective effect, while not intending to be limited to any particular mechanism of action, appears to be linked to an increase in mevalonate synthesis in the transformed cells upon treatment with Fmev. The increase in mevalonate synthesis provides for the accumulation of an as yet unidentified negative regulator of cell proliferation that is derived from mevalonate. The present inventors have found that, in such an environment, transformed cells will demonstrate a unique sensitivity to the activity of halogenated forms of mevalonate, particularly, Fmev, accumulating a larger concentration of mevalonate-derived inhibitors of DNA synthesis at low concentrations halogenated mevalonate. In contrast, normal cells are likely to be unaffected by Fmev, particularly at the range of concentrations that inhibit oncogenic Ras function.

A second theory regarding the observation of this phenomenon in malignant cells may be that malignant cells require prenylation of proteins, such as Ras protein, for proliferation. In this regard, the inventors have observed that Fmev inhibits prenylation, yet does not affect the growth of normal lymphocytes. Fmev and other di and mono-halogenated mevalonate derivatives may therefore be useful in controlling the growth of tumors dependent on Ras function, since it inhibits prenylation of Ras. As used in the definition of the present invention, the term prenylation is defined as enzymatic addition of 15-carbon farnesyl or 20-carbon geranylgeranyl lipids to the carboxy-terminal cysteine residue(s) of protein(s).

In addition, since different normal and transformed cells may require mevalonate for separate functions, detailed evaluation of possible variations in metabolism between normal and malignant cells using mevalonate will also be provided with the present invention, as the phenomenon of enhanced sensitivity of malignant cells to 6-halogen substituted forms of mevalonate, such as Fmev, disclosed by the present inventors, may be employed in embodiments of the invention to methods of developing as well as screening drugs for the treatment of tumor cells in vivo, as well as for post-cancer surgery drugs. Accordingly, the present invention provides for a pharmaceutical preparation for treating ras-transformed oncogenic tumors. The preparations comprise as an active ingredient a therapeutically effective concentration of a mono or di halogen substituted mevalonate derivative, particularly fluoromevalonate, in a pharmaceutically acceptable carrier. While biologically active equivalent preparations of fluoromevalonate and other halogenated mevalonate preparations may be used in the practice of the claimed invention, 6-fluoromevalonate (a mono-6-fluorinated mevalonate) is a particularly preferred form of the drug in conjunction with the described methods.

The claimed preparations may be formulated in any of a number of forms suitable for administration to an animal or, most specifically, for human use. By way of example, the preparation may be formulated as a tablet, capsule, parenteral formulation, or injectable preparation according to those techniques well known to those of skill in the art. For example, conventional techniques for tableting, capsulation, parenteral formulation and the like are described in Remington's Pharmaceutical Sciences (15th ed., pgs. 1488–1501, Mack Publishing Co., Easton, Pa., 1991). This reference is specifically incorporated herein in pertinent part for this purpose.

Preparations of the halogenated mevalonate derivatives, such as fluoromevalonate, in tableted form will most preferably include a concentration of between 25 mg and about 250 mg of the mevalonate preparation as within the tableting carrier preparation. Preferably, the concentration of halogenated mevalonate as part of the tablet according to the claimed invention will include about 100 mg of the active halogenated mevalonate ingredient.

The halogenated mevalonate preparations of the present invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a therapeutically effective concentration of the halogenated mevalonate forms of the present invention and the pharmaceutically acceptable carriers are then easily administered in a variety of dosage forms such as injectable solutions, ophthalmic solutions, orally ingestible forms, drug release capsules and the like.

For parenteral administration, solutions of the halogenated mevalonate in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The halogenated mevalonate preparations of the present invention may not only be advantageously employed for the preparation of aqueous pharmaceutical compositions for parenteral administration, as described above, but also for the preparation of pharmaceutical compositions suitable for use as orally ingestible preparations. Such solutions are of interest, for example, in the treatment of tumors or ras-sensitive cancers. Thus, for the treatment of ras-dependent tumors, a conjugate of this invention may be administered to the subject in need of treatment in a form suitable for oral ingestion prepared in accordance with conventional pharmaceutical practices. Pharmaceutical practices are described, for example, in "Remington's Pharmaceutical Sciences" 15th Edition, pages 1488 to 1501 (Mack Publishing Co., Easton, Pa.), which reference is specifically incorporated herein by reference for this purpose.

The preparation will contain a halogenated mevalonate derivative, such as Fmev, or a pharmaceutically acceptable salt thereof in a concentration from about 0.1 to about 1% by weight, preferably from about 0.25 to about 0.5 in a pharmaceutically acceptable solution, suspension or ointment. Some variation in concentration will necessarily occur, depending on the particular form of the compound employed, the condition of the subject to be treated, and the like. The attending physician may determine the most suitable concentration for the individual subject depending on these and other clinical considerations of the individual patent. The halogenated mevalonate preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in a solution preparation of a halogenated mevalonate preparation, such as Fmev, include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

One method of administration involves the encapsulation of the halogenated mevalonate, particularly Fmev, in a biocompatible coating. In this approach, the halogenated mevalonate is entrapped in a capsular coating that protects the contents from immunological responses. A preferred encapsulation technique involves encapsulation with alginate-polylysine-alginate. Capsules made employing this technique generally have a diameter of approximately 1 mm.

A variety of other encapsulation technologies have been developed that are proposed by the present inventor will be applicable to the practice of the present invention (see, e.g., Lacy et al., 1991; Sullivan et al., 1991; WO 9110470; WO 9110425; WO 9015637; WO9002580; U.S. Pat. No. 5,011, 472; U.S. Pat. No. 4,892,538; WO 8901967, each of the foregoing being incorporated by reference). The company Cytotherapeutics has developed encapsulation technologies that are now commercially available that will likely be of use in the application of the present invention. A vascular device has also been developed by Biohybrid, of Shrewsbury, Mass., that may have application to the technology of the present invention.

An additional aspect of the claimed invention include the methods for treating ras dependent tumor growth. A particularly preferred embodiment of the claimed method comprises identifying a tumor having an oncogenic ras mutation and treating the tumor with a therapeutically effective amount of a halogenated mevalonate preparation, such as fluoromevalonate or a biologically equivalent derivative thereof. Most preferably, the fluoromevalonate is 6-fluoromevalonate.

As used in the description of the present invention, the term "biologically equivalent derivative thereof" relates to compositions which include the biologically active characteristics of 6-fluoromevalonate or inhibitors of mevalonate, i.e., the ability to specifically inhibit tumor growth of oncogenic ras dependents at low concentrations while allowing for normal non-oncogenic ras cell growth.

As used in the description of the present invention, the term "therapeutically effective amount" is defined as an amount of the active ingredient sufficient to inhibit oncogenic ras tumor growth. While the specific amounts and concentrations of the active ingredient that will affect this selective and potent inhibitory activity will vary, it is contemplated that doses of between about 1 mg/kg and about 50 mg/kg of the halogenated mevalonate, particularly Fmev, will be effective in the treatment of ras dependent tumor when used as part of a treatment regimen.

By way of example, the claimed method may be employed in the treatment of ras dependent tumor growth known as the adenocarcinomas. As already described, oncogenic ras dependent tumor growth is characteristic of some 20% of all human cancers. By way of example, such include the lung cancers, and colon cancer. (See Table 2, BOS, (1988), *Mut. Res.*, 195:225–271, specifically incorporated herein by reference for this purpose). Thus, the claimed method may be most expeditiously used in the treatment of these cancers. The claimed method has been shown to be particularly efficacious in the inhibition of Ras-transformed tumor cell growth. For example, the results presented in the present disclosure demonstrate a marked inhibition of in vivo tumor cell growth with Fmev.

The claimed invention also provides for methods of inhibiting ras-dependent cancer growth in a patient. This method comprises identifying a patient having an oncogene ras-dependent cancer; and treating the patient with a therapeutically effective amount of a halogenated mevalonate preparation, particularly fluoromevalonate. Again, while the therapeutically effective concentration of the mevalonate preparation may vary, depending upon the status of the cancer patient, the location and type of cancer growth, and the like, it is anticipated that a therapeutically effective concentration would fall between dosage levels of between about 1 mg/kg and about 50 mg/kg for the effective inhibition of continued cancer growth. It is anticipated that the claimed method may be employed in the inhibition of, for example, lung cancer progression in a patient. Generally, however, the methods may be employed for inhibiting virtually any group of ras mutation-related cancers, (see, e.g., Table 2 of Bos, 1988, incorporated herein by reference), such as, for example, adenocarcinomas and leukemias.

In a related aspect, the present invention also provides for an in vitro method for selectively inhibiting oncogenic ras-dependent cell growth without the inhibition of non-oncogenic ras-dependent cell growth. Thus, the method finds particular application for use in purging a mixed population of cells of oncogenic ras-cell dependent cells. Such application would be particularly advantageous, for example, in the preparation of an autologous bone marrow transplant for a leukemia patient. As part of such a method, the bone marrow sample from a leukemia patient would be first withdrawn and then treated with a pharmacologically effective amount of a halogenated mevatonate, such as fluoromevalonate, or a biologically active equivalent thereof. Most preferably, of course, the fluoromevalonate is 6-fluoromevalonate. Thus, the method provides an effective and selective method for the treatment of leukemia, as autologous bone marrow samples are rendered essentially, ras oncogene cell free prior to autologous bone marrow transplant.

The present in vivo studies provided by the inventors demonstrate that the use of fluoromevalonate in vivo is not toxic. The selective inhibition of halogenated forms of mevalonate, particularly fluoromevalonate, to oncogenic-ras-transformed cells, highlights an important feature of the present invention. That is, the growth inhibition of ras-dependent cells is shown to be specifically selective for the leukemic population of cells, while surprisingly, and of great benefit, leaving the normal population of non-oncogenic ras-transformed cells unaffected in terms of viability and proliferation capabilities. The inventors demonstrate the selective, ras-transformed cell directed inhibiting effects in the presence of serum. These effects may also be demonstrated in serum-free-media as only cholesterol is important in the selective, ras-transformed cell activity of the directed inhibiting effects of halogenated mevalonate preparations. Thus, the present invention provides a most practical system for purging human bone marrow samples of leukemic patients. In this regard, the claimed method provides an attractive and advantageous alternative to conventional chemotherapeutic treatment.

Unfortunately, as known to those of skill in the art, chemotherapeutic treatment of leukemic patients, for example, with daunomycin AraC, or GMCSF, typically result in a significant reduction in normal cell (i.e., non-ras-transformed cells) growth and viability. The fluoromevalonate of the present invention, has been demonstrated by the present inventors to leave virtually unaffected this normal population of cells, both in vivo and in vitro. Therefore, by employing the claimed methods, a sample may be purged of oncogenic ras cells while providing an enriched population of normal oncogenic ras-transformed cells to the patient through the use of Fmev and other mono and di-halogenated forms of mevalonate.

Generally stated, the present invention provides a method of treating leukemia in a patient comprising preparing an essentially leukemia cell-free, autologous bone marrow sample by treating the bone marrow sample with a therapeutically effective concentration of halogenated mevalonate and administering the treated essentially leukemia cell-free autologous bone marrow sample to the patient. Again, the most preferred halogenated forms of mevalonate are mono- and di-substituted fluoro mevalonate preparations.

For the purpose of this invention, an autologous bone marrow sample is defined as a sample of bone marrow from the patient to be treated. In a most preferred embodiment, the present invention provides a method for treating leukemia in a patient comprising the following steps: preparing a therapeutically effective amount of a halogenated mevalonate; obtaining a bone marrow sample from a patient having a ras-oncogene-dependent leukemia; treating the bone marrow sample with a pharmacologically active amount of the halogenated mevalonate, said amount being effective to kill leukemia cells, for a period of time sufficient to provide an essentially leukemia cell-free bone marrow sample, and administering the essentially leukemia cell-free bone marrow sample to the patient to provide a treatment for leukemia. In particular, selective cell killing may be achieved with concentrations of fluoromevalonate of between about 10 to about 100 µM. The reduction in oncogenic Ras-transformed leukemic cells destroyed relative to normal bone marrow cells is estimated to be between about $10^3$ and about $10^6$.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A: Inhibition of the incorporation of [$^3$H] mevalonolactone into all proteins in FDC-P1 and RasDC cells by increasing concentrations of Fmev. Cells were incubated and processed as described above. Protein fractions were separated by SDS-polyacrylamide gel electrophoresis and visualized by fluorography (Cuthbert and Lipsky, 1990). FIG. 4B: Fmev inhibition of protein prenylation in RasDC cells is unaltered by exogenous IL-3 (interleukin-3). Cells were incubated and processed as described above. Protein fractions were separated and visualized as described above. Representative fluorogram of 3 studies.

FIG. 7A panel: RasDC cells (5,000 cells/microtiter well) were incubated in complete medium with 5 μM lovastatin (to prevent accumulation of a mevalonate-derived inhibitor), varying concentrations of Fmev and with or without 5% WEHI-3 supernatant as indicated. Cellular DNA synthesis was quantitated after 4 days (Cuthbert and Lipsky (1990)). Results are mean ±SEM of triplicate determinations from one of 3 similar studies. FIG. 7B panel: RasDC cells (500 cells/microtiter well) were incubated in complete medium with 5 μM lovastatin, with or without Fmev (500 μM) and with or without exogenous IL-3 (recombinant murine IL-3, (DNAX) or 5% WEHI-3 supernatant) as indicated. The DNAX company produced the IL-3 (interleukin-3) used in the study of the present invention. DNA synthesis was measured after 5 days by the incorporation of [$^3$H] thymidine. Results are mean ±SEM of triplicate determinations.

FIGS. 8A and 8B—K-ras Mutations in Lung Cancer Cell Lines Alter Responses to inhibitors of Protein Prenylation. This figure contains two panels, FIG. 8A and 8B. H187 (small cell lung cancer-derived; normal codon 12 (GGT) K-ras) and H157 (non-small lung cancer derived; activating codon 12 mutation (GT-CGT) in K-ras) lung cancer cell lines (5,000 cells/microtiter well) were incubated in RPMI-1640 basal medium supplemented with 10% fetal bovine serum and with or without varying concentrations of Fmev and lovastatin (0.5 μM) as indicated. Cellular DNA synthesis was quantitated after 4 days (H157 lung cancer cells) or 7 days (H187 lung cancer cells) by the incorporation of [$^3$H] thymidine as described by Cuthbert & Lipsky (1991). Results are mean ±SEM of triplicate determinations.

DETAILED DESCRIPTION OF THE PREFERRED EMBODIMENTS

Figure 1:
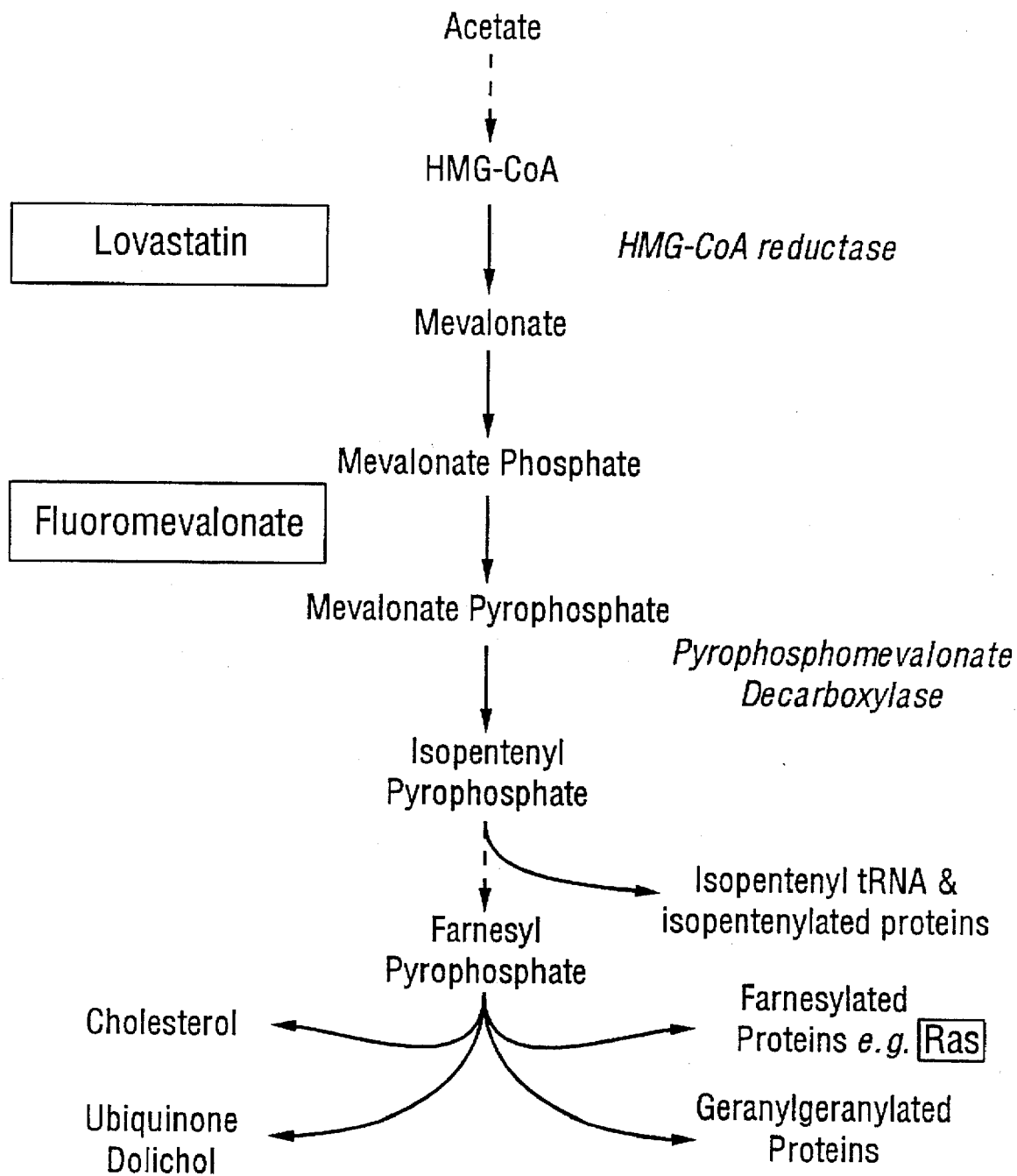
FIG. 1—Endogenous synthesis of mevalonate and its sterol and non-sterol products.

The present invention provides methods and preparations for the treatment and inhibition of tumor cell proliferation, both in vitro and in vivo, such as in the treatment of human cancer.

Cancer cells and normal cells differ in many ways, one of which is in the biosynthetic regulation of lipids, particularly cholesterol. Thus, in normal cells, cholesterol metabolism is tightly regulated by the balance between input (from endogenous synthesis and uptake of exogenous cholesterol in lipoproteins) and output, reviewed in Goldstein and Brown, (1990). Both endogenous synthesis and the uptake of exogenous lipoproteins are controlled by transcriptional regulation of the expression of the appropriate genes, those encoding HMG-CoA reductase and the cell surface receptor for low density lipoprotein (LDL). Mevalonate, the product of HMG-CoA reductase activity, is not only the endogenous precursor of cholesterol, but is also a precursor of other products, including certain tRNAs, the lipids dolichol and ubiquinone, and proteins post-translationally modified by the covalent linkage of mevalonate-derived prenyl groups.

The exact role of de novo synthesis of these products from mevalonate in the function of different normal cells has not been elucidated. Of particular importance, one or more of these products, or another as yet unidentified product of mevalonate metabolism, is essential for continuing proliferation of all cells (Kaneko et al., 1978; Goldstein & Brown, 1990). Furthermore, while both mevalonate and the end-product of mevalonate metabolism, cholesterol, are necessary for normal cellular growth and function, accumulation of mevalonate or one of its intermediate metabolites is also capable of inhibiting the growth of a variety of cells (Cuthbert and Lipsky, 1991; Faust and Krieger, 1987). Thus, mevalonate is a source or precursor of a naturally-occurring negative regulator of cell growth. Normal cell growth and proliferation is likely to reflect the balance between the positive and negative influences of mevalonate.

The present invention provides methods and compositions for inhibiting tumor cell proliferation which have also utility in the treatment of cancer. The compositions and preparations of the invention include as an active ingredient fluoromevalonate (Fmev). This agent is demonstrated to have selective and potent tumor-inhibiting activity, as it selectively inhibits the growth of tumors which include a mutation that activates the ras-oncogene, a mutation that is characteristic of about 20% of all human tumors and cancers.

The utility of the claimed method for reducing tumor growth in vivo is demonstrated herein in a widely accepted animal model. For example, when mice were treated with a single injection of 6-fluoromevalonate, tumor growth was observed to be suppressed by 95–98%. While not intending to be limited to any particular mechanism of action, the inventors contemplate that the ability of a single injection of 6-fluoromevalonate to be effective is likely related to the capacity of 6-fluoromevalonate to inhibit mevalonate metabolism irreversibly. Additional in vitro data have demonstrated that initial incubation with 6-fluoromevalonate renders cells irreversibly inhibited unless alternative growth pathways are signalled.

The effectiveness of 6-fluoromevalonate in vivo is contemplated by the inventors to be related to the depletion of total Ras demonstrated in vitro. It is therefore envisioned that many cancer cells may be peculiarly sensitive to 6-fluoromevalonate inhibition because of the presence of abnormalities in regulation of mevalonate synthesis. Normal cells may be protected from such effects by tightly controlled regulatory mechanisms.

In vitro systems for purging ras-transformed cells are also provided by the present invention. In this regard, the inventors have shown that exposure of ras- oncogene transformed cells to relatively low concentrations of the Fmev effectively prevents proliferation of these cells, and eventually provides for the elimination of these cells in vitro. As the low concentrations of Fmev have also been shown by the inventors to not inhibit non-ras oncogene transformed cells, the in vitro system would be ideal for purging mixed transformed and normal cell populations, such as that characteristic of bone marrow tissue from leukemia patients. After treatment with the Fmev, the tissue purged of the ras oncogene transformed cells may be used as an autologous bone marrow transplant in the leukemia patient.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

FLUOROMEVALONATE AND CELL GROWTH

The nature of the non-sterol product of mevalonate was examined by the present inventors using 6-fluoromevalonate (Fmev), a potent inhibitor of the activity of pyrophosphomevalonate decarboxylase (FIG. 1). Fmev was synthesized by PM Laboratory, Plano Tex. This inhibitor differs from lovastatin in that it does not inhibit the synthesis of mevalonate but does prevent generation of all products of mevalonate metabolism distal to and including isopentenyl pyrophosphate. In contrast to lovastatin, the present inventors demonstrate that Fmev does not block proliferation of normal cells if cholesterol is provided (Cuthbert & Lipsky, 1990). These results indicate that the product of mevalonate required for cell growth is directly synthesized either from mevalonate or one of its phosphate derivatives. The finding that Fmev blocked prenylation of all newly-synthesized proteins but did not inhibit proliferation of fresh cells or a number of cell lines indicated that ongoing lipid modification of Ras may not be necessary for growth of normal cells or even some transformed cell lines.

In transformed cells, Fmev inhibited cell growth by causing the accumulation of mevalonate or its phosphates. This was related to the diminished regulation of HMG-CoA reductase activity by LDL cholesterol that is characteristic of many transformed cells. Inhibition could be overcome by low concentrations of lovastatin. In normal cells, down-regulation of HMG-CoA reductase activity by exogenous LDL cholesterol was sufficient to prevent the activity of the inhibitory by-product.

EXAMPLE 2

FLUOROMEVALONATE AND ONCOGENIC RAS

Even though prenylation did not appear to be necessary for the growth of normal cells, it remained possible, however, that cells transformed by oncogenic Ras would uniquely require protein prenylation and that Fmev would selectively inhibit their growth. The present study demonstrates that Fmev suppresses prenylation and Fmev membrane association of Ras and thus specifically inhibits the growth of cells whose autonomous proliferation was driven by Ras.

To determine whether inhibition of prenylation would block proliferation of cells transformed by oncogenic Ras, Fmev was used to prevent the synthesis of prenylated proteins in control, interleukin-3 (IL-3)-dependent, FDC-P1 cells (Factor-Dependent Continuous cell line, Paterson laboratories) and FDC-P1 cells transformed with oncogenic Ras (Ras-Dependent Continuous cell line, RasDC) that proliferated in the absence of IL-3. The control, IL-3-dependent FDC-P1 cells and the RasDC cells were obtained from H. Scott Boswell, and may also be obtained following the protocols described in Boswell et al., 1990, incorporated herein by reference.

Cells, cultured in complete medium (RPMI-1640 and 10% iron-supplemented calf serum) containing 5% v/v 10× WEHI-3 supernatant, 5µM lovastatin, and varying concentrations of Fmev as indicated were incubated for 24 hours with [5-$^3$H] mevalonolactone (specific activity 27.8 Ci/mmol). Following extensive washing, cells were solubilized and separated into lipid and protein fractions. Incorporation of radiolabeled mevalonolactone into lipid (●) and protein (▲) products was then quantified (DeClue et al., 1991). The results from these studies are provided as FIGS. 2 and 2B.

Fmev completely inhibited protein prenylation, depleted total cellular and membrane-associated Ras and blocked IL-3-independent proliferation of RasDC. However, both control FDC-P1 and RasDC cells proliferated in response to IL-3 when prenylation was inhibited by Fmev. These results indicate that growth of cells transformed by oncogenic Ras can be specifically prevented by Fmev and therefore indicate that this approach would be suitable for treating tumors induced by oncogene products requiring prenylation for activity.

EXAMPLE 3

EFFECT OF Fmev ON Ras-TRANSFORMED FDC-P1 CELLS

Proliferation of untransformed FDC-P1 (Factor-Dependent Continuous cell line, Paterson laboratories) cells is dependent on the exogenous growth factor IL-3. However, when transformed with oncogenic Ras, cell growth becomes IL-3 independent. The effect of blocking mevalonate metabolism with Fmev on the Ras-transformed FDC-P1 cell line FI Neo Ras.G4 (Ras-Dependent Continuous cell line, RasDC), that has been transfected with a mutant (valine codon 12) human H-ras genomic clone derived from the T24 bladder carcinoma is examined in the present example. These studies were conducted as described in the detailed description of the drawings sections which correspond to the particular figures cited hereinbelow.

Figure 2A:
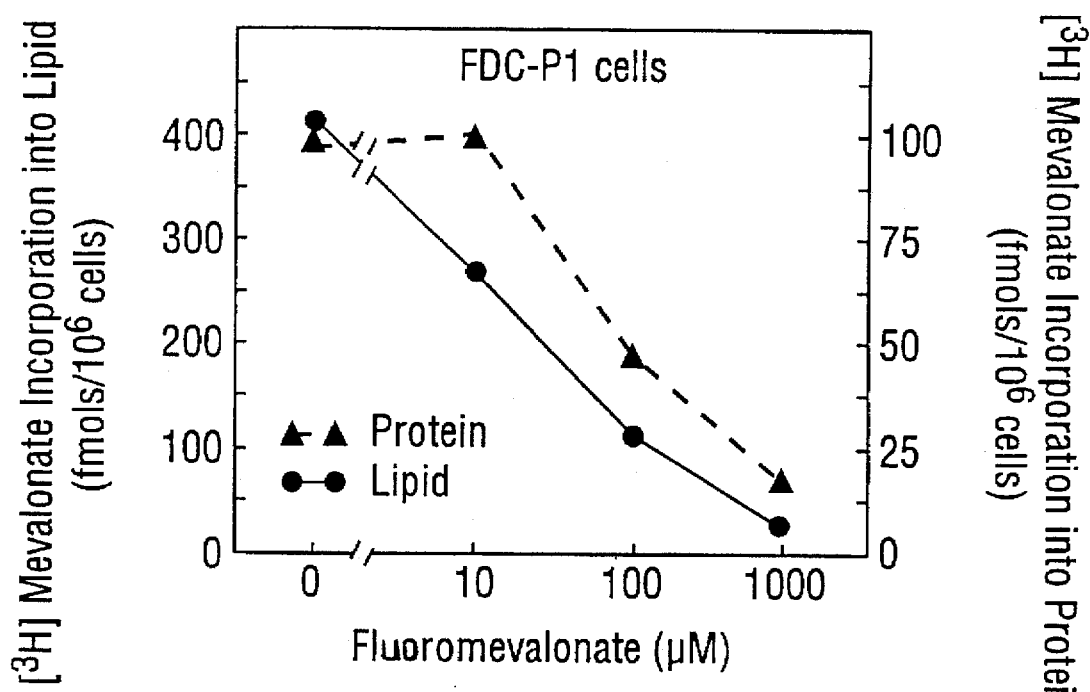
FIG. 2A and 2B—Fluoromevalonate inhibits mevalonate metabolism in FDC-P1 cells (Factor-Dependent Continuous cell line, Paterson laboratories), Upper panel, and RasDC (Ras-Dependent Continuous cell line) cells, Lower panel. This figure contains two panels, upper and lower. Inhibition of the incorporation of [$^3$H] mevalonolactone into lipid and protein in FDC-P1 (Upper panel) and RasDC cells (Lower panel) by increasing concentrations of Fmev. Cells, cultured in complete medium (RPMI-1640 and 10% iron-supplemented calf serum) containing 5% v/v 10× WEHI-3 supernatant, 5 µM lovastatin, and varying concentrations of Fmev as indicated were incubated for 24 hours with [5-$^3$H] mevalonolactone (specific activity 27.8 Ci/mmol). Following extensive washing, cells were solubilized and separated into lipid and protein fractions. Incorporation of radiolabeled mevalonolactone into lipid (●) and protein (▲) products was then quantified (Cuthbert & Lipsky, 1990).
Figure 2B:
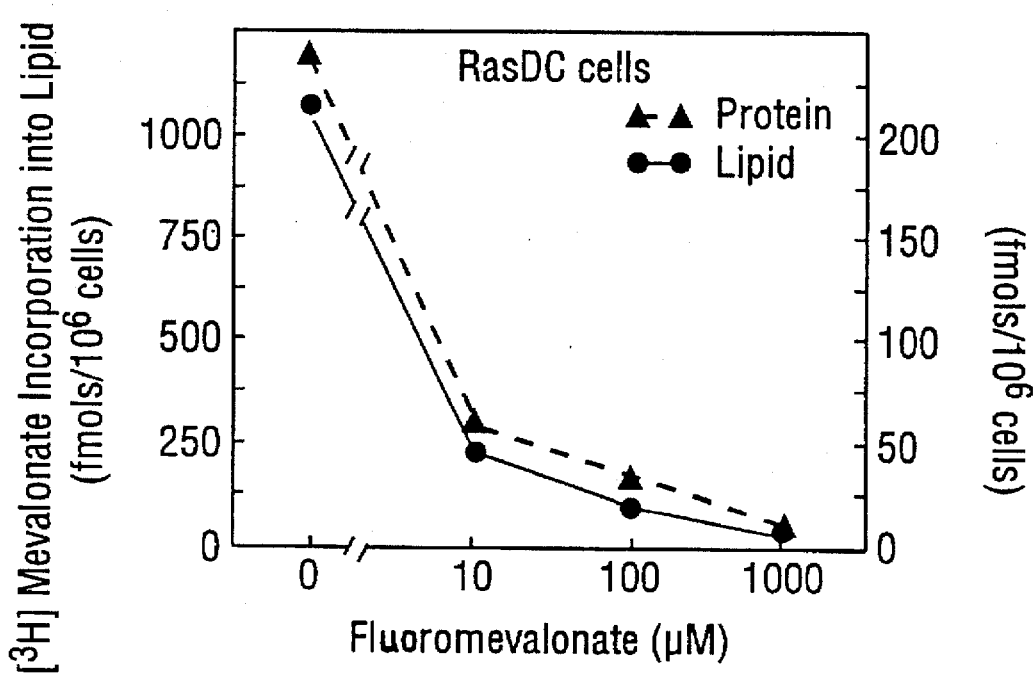
Figure 3:
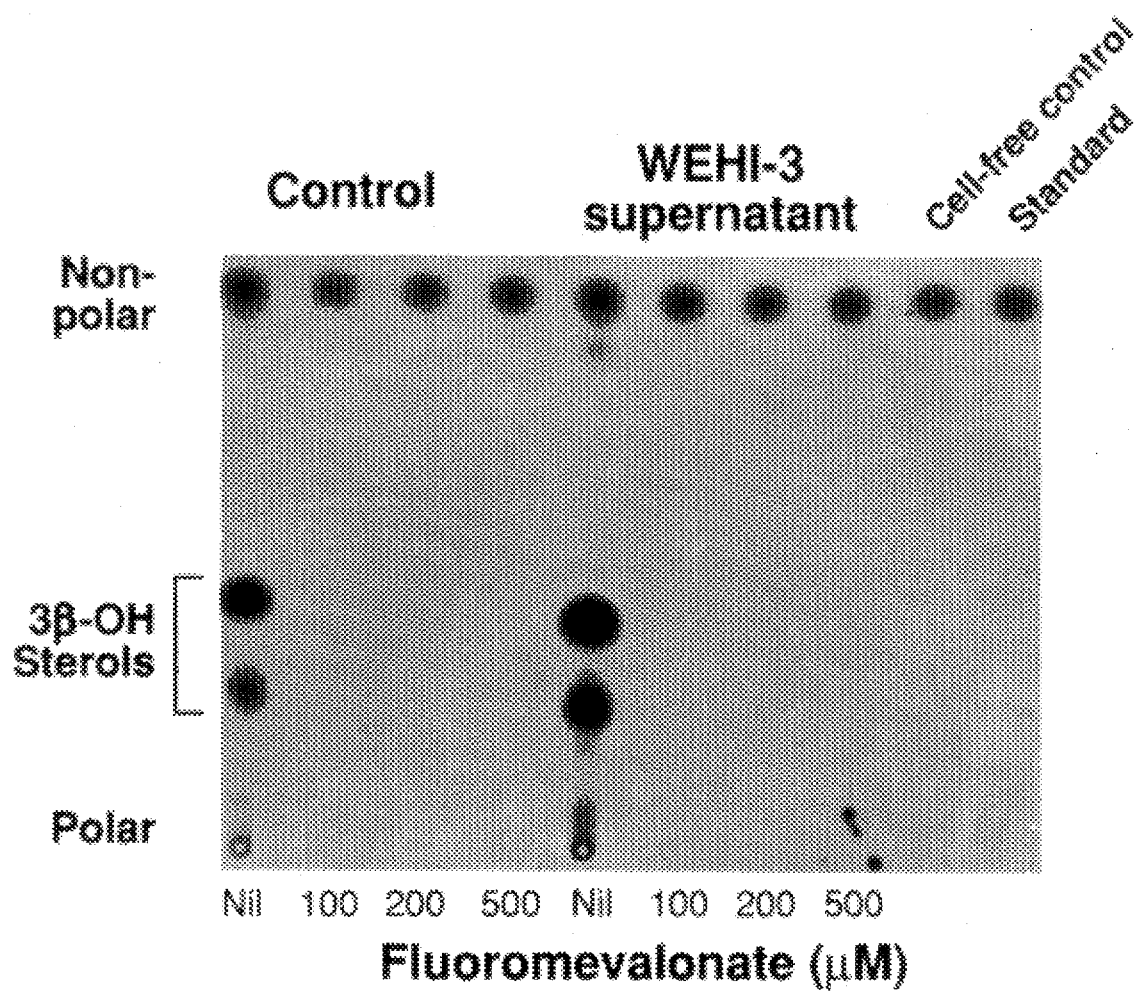
FIG. 3—Fmev inhibits the incorporation of radiolabeled mevalonolactone into all lipid products in RasDC cells. RasDC cells, cultured in complete medium containing 5 µM lovastatin, varying concentrations of Fmev as indicated as without (lanes 1–4) or with (lanes 5–8) 5% WEHI-3 supernatant, were incubated with [5-$^3$H] mevalonolactone for 24 hours. Cells were processed as described above, the lipids separated by thin-layer chromatography, identified by comparison with iodine-stained authentic standards, visualized by fluorography and quantitated by liquid scintillation spectroscopy, using recovery of [$^{14}$C] cholesteryl ester to correct for any procedural losses. Representative fluorogram of 3 studies with comparable results.
Figure 4A:
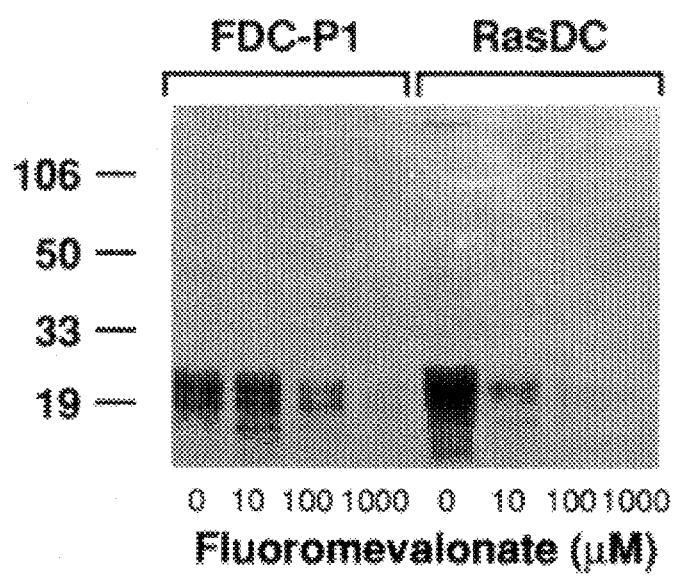
FIGS. 4A and 4B—Inhibition of mevalonate incorporation into lipids and proteins by Fmev. Prevention of prenylation of Ras by Fmev. This figure contains two panels FIG. 4A and FIG. 4B.
Figure 4B:
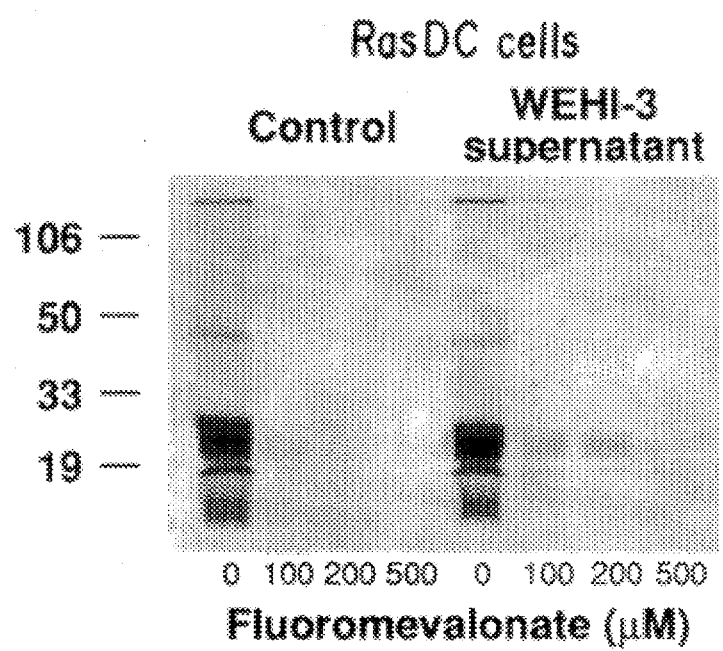

Fmev inhibited the incorporation of 5-[$^3$H] mevalonate into lipids and protein in a concentration-dependent manner (FIG. 2). Fluorography of [$^3$H] mevalonate-labeled lipids and proteins, separated by thin-layer chromatography and sodium dodecyl sulfate-polyacrylamide gel electrophoresis respectively, demonstrated that Fmev completely suppressed not only the incorporation of [$^3$H] mevalonate into all lipids (FIG. 3) but also the prenylation of Ras and all other proteins (FIGS. 4A and 4B). The addition of 500 µM Fmev suppressed [$^3$H] mevalonate incorporation into protein by 97.4±0.5% (mean±SEM, n=3). Thus, Fmev effectively blocked the post-translational processing of all proteins with farnesyl or geranylgeranyl lipids.

Inhibition of protein prenylation by Fmev also decreased both membrane-associated and total cellular Ras. For these studies, Fmev (500 µM) was compared with a concentration of lovastatin (50 µM) that produced similar inhibition of mevalonate metabolism (control (untreated) cells 135.9±2.8 pmols [1-$^{14}$C] acetate incorporated into digitonin-precipitable sterols/hr/10$^6$ cells; fluoromevalonate 4.9±0.3 pmols/hr/10$^6$ cells; lovastatin 1.4±0.7 pmols/hr/10$^6$ cells). After a 48 hour incubation, RasDC cells cultured with 500 µM Fmev or 50 µM lovastatin were separated into soluble (cytosolic) and particulate (membrane) fractions and Ras was detected by immunoblotting.

Figure 5:
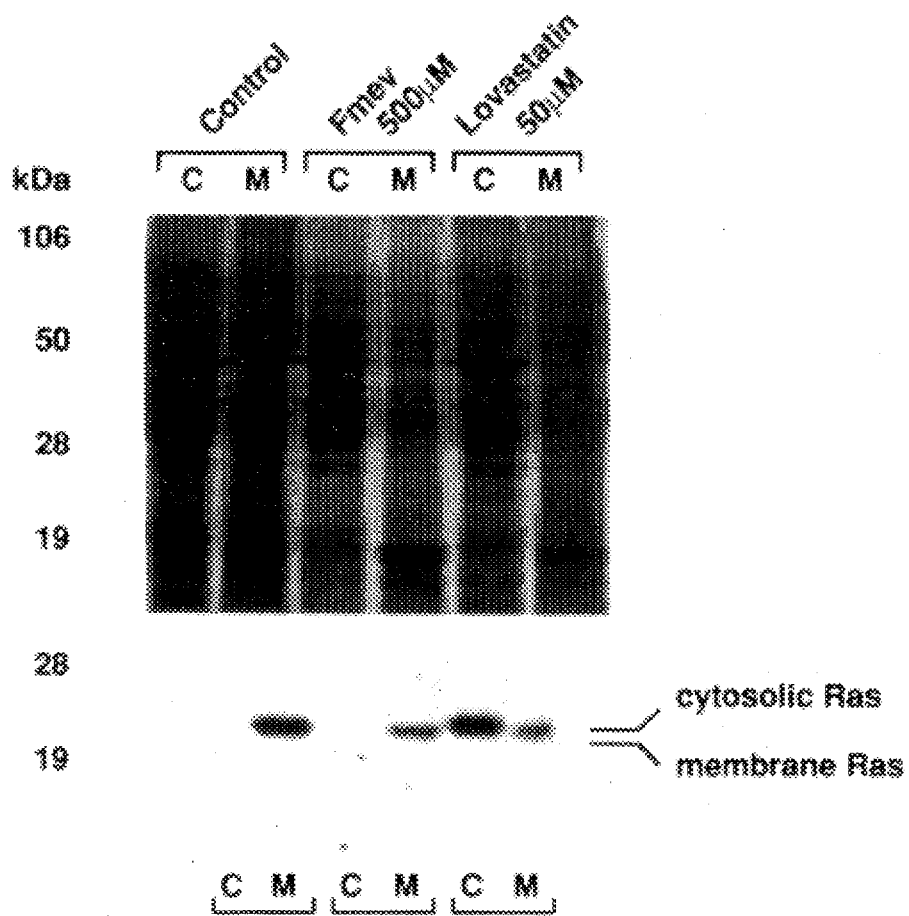
FIG. 5—Fmev depletes membrane-associated Ras. This figure contains two panels, upper and lower. RasDC cells, incubated for 48 hrs in complete medium with or without 500 μM F meu and 50 μM lovastatin as indicated, were separated into soluble (S) and particulate (P) fractions by 100,000 g centrifugation after homogenization in hypotonic buffer and removal of nuclei by low-speed centrifugation (Cuthbert & Lipsky, 1991). Proteins separated by sodium dodecyl sulfate-polyacrylamide gel electrophoresis were transferred to nitrocellulose membranes and Ras proteins identified by immunoblotting with mouse monoclonal anti-ras antibody LA045 (Niman, 1986; Chesa et al., 1987) and detecting bound antibody with affinity-purified horse radish peroxidase-conjugated goat anti-mouse IgG and enhanced chemiluminescence (ECL, Amersham International, UK). The samples were also separated by SDS-PAGE and the gels were stained for protein with Coomassie blue. Upper panel: Coomassie blue stain of SDS-PAGE gel. Lower panel: fluorogram demonstrating localization of Ras.

Fmev and lovastatin were found to cause a similar diminution in membrane-associated Ras in RasDC cells. In lovastatin-blocked RasDC cells, but not Fmev-blocked cells, there was accumulation of Ras in the cytoplasm (FIG. 5, lower panel). Of note, Fmev caused a marked depletion of cytoplasmic as well as membrane Ras with a resultant striking diminution in total cellular Ras. Total cytosolic and membrane proteins were largely unaffected by either lovastatin or Fmev (FIG. 5, upper panel). These results indicate that Fmev not only effectively prevents the post-translational modification of proteins by prenylation but also blocks the localization of Ras to the membrane.

EXAMPLE 4

Fmev AND RAS-DEPENDENT PROLIFERATION OF FDC-P1 CELLS AND Ras DC CELLS

Figure 6A:
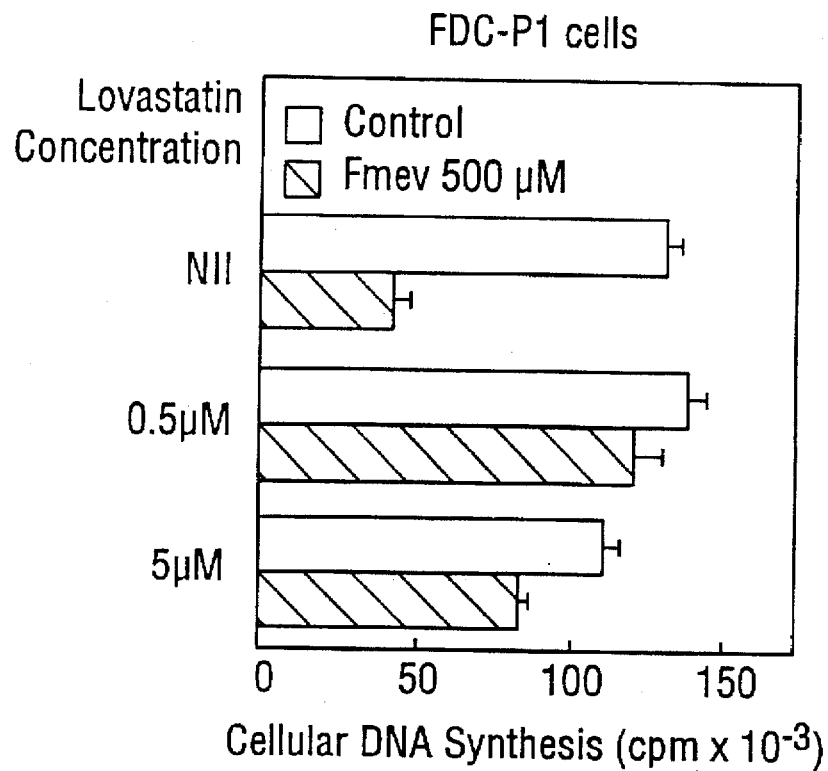
FIGS. 6A and 6B—Lovastatin restores proliferation of Fmev-blocked FDC-P1 cells but not RasDC cells. This figure contains two panels, FIG. 6A (FDC-P1) and FIG. 6B (RasDC). FDC-P1 and RasDC cells (5,000 cells/microtiter well) were incubated in complete medium with (FDC-P1) or without (RasDC) 5% WEHI-3 supernatant. Fmev (500 μM) and varying concentrations of lovastatin were added as indicated. After 4 days, cellular DNA synthesis was quantified by the incorporation of [$^3$H] thymidine as detailed (Cuthbert JA and Lipsky PE, (1990)). Results are mean ±SEM of triplicate determinations from a study that is representative of 3 similar studies.
Figure 6B:
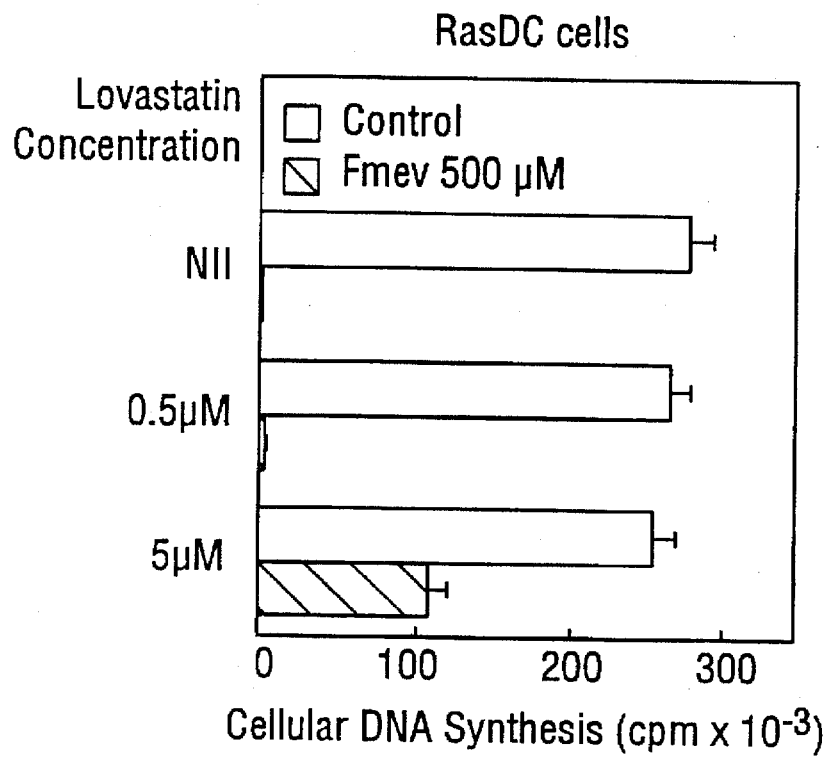

To examine the effect of Fmev on proliferation of Ras-transformed cells, control FDC-P1 and RasDC cells were cultured in lipoprotein-containing medium, to provide the cholesterol necessary for membrane synthesis in Fmev-blocked cultures. It was found that Fmev (500 µM) inhibited DNA synthesis by control FDC-P1 cells by 68% (FIG. 6A). Blocking mevalonate synthesis with a low concentration of lovastatin completely reversed the suppressive effect of Fmev, demonstrating that this Fmev-mediated inhibition was the result of accumulation of a mevalonate-derived inhibitor in Fmev-blocked cells, as has been previously described and not the result of inhibition of prenylation. Lovastatin, at the concentration utilized, did not decrease mevalonate synthesis sufficiently to affect proliferation of these cells. In contrast to the effect noted with the parent cell line, Fmev (500 µM) completely suppressed DNA synthesis by the RasDC cells (FIG. 6B). This inhibitory effect of Fmev was only partially prevented by lovastatin.

The above results indicate that Fmev suppressed cellular proliferation by two mechanisms when exogenous cholesterol was provided. One mechanism was dependent on the accumulation of mevalonate and/or mevalonate phosphates. This occurred in both untransformed and Ras-transformed cells and could be overcome by decreasing mevalonate synthesis with low concentrations of lovastatin. In contrast, the second effect of Fmev was limited to the Ras-transformed cells, was not prevented by lovastatin and therefore was potentially the result of interference with protein prenylation.

Figure 7A:
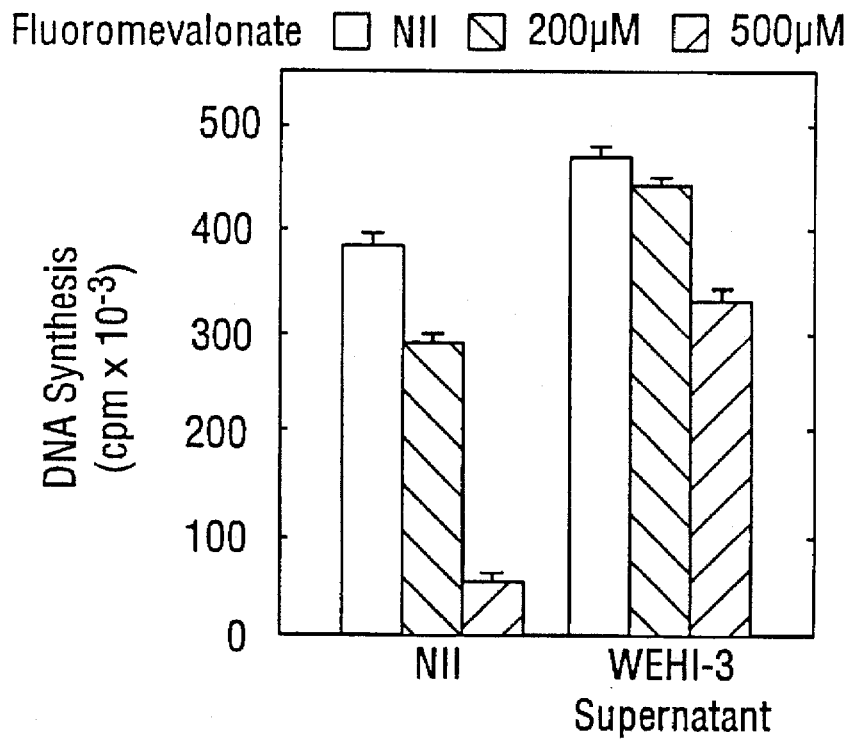
FIGS. 7A and 7B—Exogenous IL-3 restores proliferation of Fmev-blocked RasDC cells. This figure contains two panels, FIG. 7A and 7B.
Figure 7B:
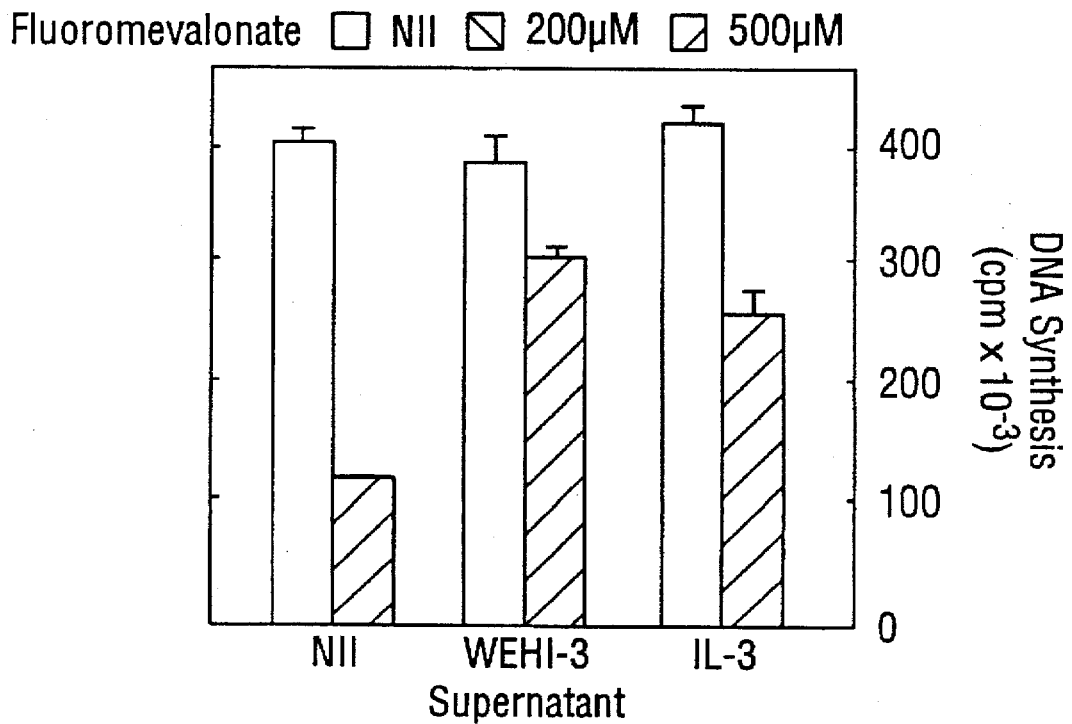

Whether this additional effect of Fmev could be negated by provision of exogenous growth factors was next examined. The RasDC cells were grown in lipoprotein-containing medium and cultures were supplemented with sufficient lovastatin (5 µM) to prevent the accumulation of an inhibitory product of mevalonate in the Fmev-blocked cells. RasDC cells proliferated in the absence of exogenous growth factors. As noted above, Fmev suppressed this growth in a concentration-dependent manner (FIG. 7a). Supplementation of the cultures with exogenous, IL-3-containing culture supernatants largely prevented the inhibitory effects of Fmev. Both recombinant murine IL-3 produced by DNAX and medium conditioned by the cell-line WEHI-3 ATCC #TIB 68 and containing IL-3 were able to restore growth to Fmev-blocked RasDC cells (FIG. 7b).

Of importance, Fmev inhibited the synthesis of prenylated proteins comparably in the presence and absence of exogenous IL-3 (see FIGS. 4A and 4B). These findings demonstrate that inhibition of protein prenylation with Fmev suppressed factor-independent proliferation of Ras-transformed cells. Proliferation supported by exogenous interleukin-3 was unaffected by Fmev-mediate inhibition of protein prenylation, indicating that Fmev was not non-specifically altering their proliferative ability or capacity to respond to IL-3.

EXAMPLE 5

INHIBITORY EFFECT OF Fmev ON OTHER RAS-TRANSFORMED CELLS

The present example demonstrates the ability of Fmev to inhibit the growth of other cell lines containing oncogenic Ras mutations. For these studies, the inventors used lung cancer cell lines with normal or mutated H-, K-, and N-ras genes. These cell lines included H187 cells (Miller et al. 1989)[24], J Cline Invest, 83:2120–2124; H157 Mitsudomi (1991)[25]. Lung cancer cell lines were grown in lipoprotein-containing medium and the ability of Fmev to inhibit cell proliferation was determined by measuring DNA synthesis. Measurement of DNA synthesis is described by Cuthbert and Lipsky, (1991), which reference is specifically incorporated herein by reference of this purpose.

H187 (small cell lung cancer-derived; normal codon 12 (GGT) K-ras) and H157 (non-small lung cancer derived; activating codon 12 mutation (GT-CGT) in K-ras) lung cancer cell lines (5,000 cells/microtiter well) were incubated in RPMI-1640 basal medium supplemented with 10% fetal bovine serum and with or without varying concentrations of Fmev and lovastatin (0.5 μM) as indicated. Cellular DNA synthesis was quantitated after 4 days (H157 lung cancer cells) or 7 days (H187 lung cancer cells) by the incorporation of [$^3$H] thymidine as described by Cuthbert & Lipsky (1991).

Figure 8A:
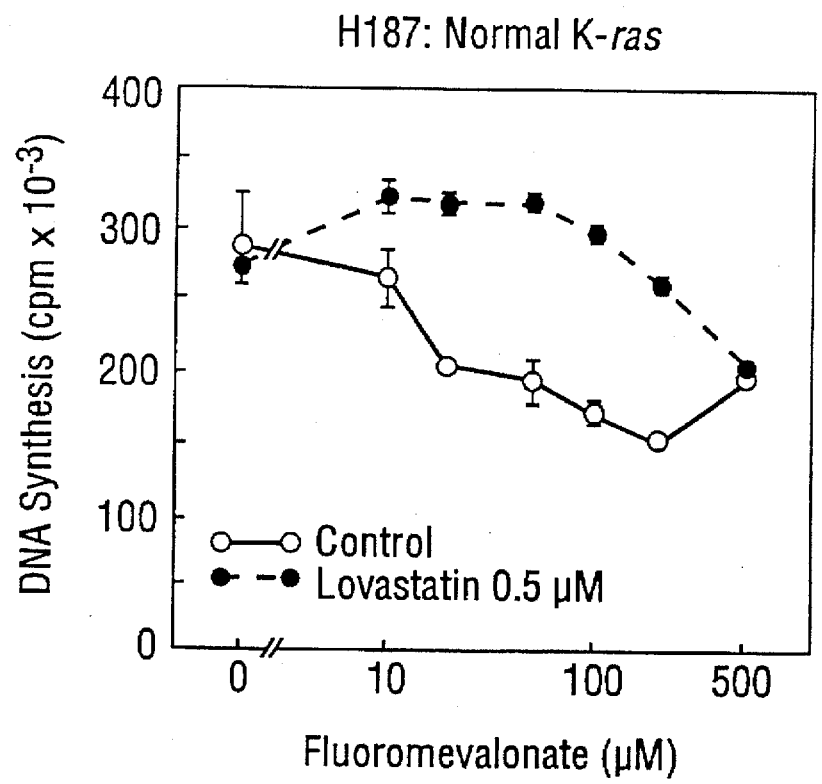
Figure 8B:
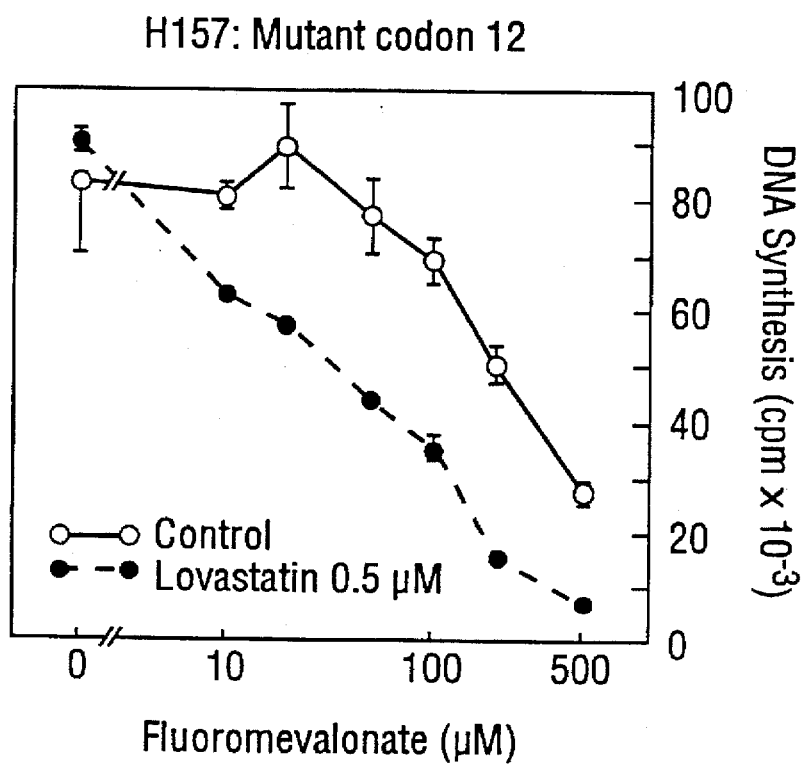

As shown in the representative studies depicted in FIGS. 8A and 8B, Fmev inhibited the growth of all cell lines in a concentration-dependent manner, regardless of the presence or absence of oncogenic ras genes. However, the inhibitory effects of Fmev were largely prevented by lovastatin when the ras genes were normal (FIG. 8B). Lung cancer cell lines with normal ras genes thus resemble transformed lymphoid and myeloid cell lines (Cuthbert and Lipsky 1991) in that they accumulate an inhibitor of proliferation when mevalonate metabolism is blocked by Fmev.

In contrast, in cell lines containing oncogenic K-ras with valine-12 mutations, the addition of lovastatin resulted in further inhibition of cell growth (FIG. 8A). These results indicate that spontaneously developing human tumors containing oncogenic Ras resemble RasDC cells in their sensitivity to Fmev and suggest that prevention of prenylation with Fmev may inhibit Ras-dependent proliferation of human malignant cells in vivo.

These results evidence that, when growth factor-independent cell proliferation requires oncogenic Ras function, prevention of prenylation blocks expression of the Ras-driven phenotype. In contrast, prenylation of normal Ras does not appear to be necessary for continued cell growth. This difference provides a novel strategy to prevent in vivo growth of Ras-transformed cells selectively.

EXAMPLE 6

FLUOROMEVALONATE INHIBITION OF TUMOR GROWTH IN VIVO

The present example demonstrates the in vivo utility of halogenated mevalonate derivatives for inhibiting RAS-dependent tumor growth.

The present in vivo studies were conducted in nude mice and DBA/2 mice to investigate whether Fmev may block the growth of RasDC cells in vivo.

In nude mice, subcutaneous injection of ≧2×10$^6$ RasDC cells resulted in demonstrable progressive tumor growth by one week in 5/5 mice. At sacrifice after 2–3 weeks, tumors weighted 1–2 g. The parent cell line, FDC-P1, was derived from DBA/2 bone marrow.

DBA/2 mice (syngeneic for RasDC cells since FDC-P1 parental cell line derived from DBA/2 bone marrow) were injected subcutaneously on the back with 10×10$^5$ RasDC cells. Some of the mice received a total of 10 μmols Fmev parenterally (intra-peritoneal or intravenous) at the same time. After three weeks, mice were sacrificed and the tumors dissected and weighed. The tumor in the control mouse (left) weighed 2.7 grams, the tumor in the Fmev-treated mouse (right) weighed 0.05 grams. Similar results were obtained in another Fmev-treated animal (tumor weight 0.1 grams). The tumor in the treated mice was decreased in size by 96–98%. These findings suggest that Fmev is effective at inhibiting the growth of Ras-transformed cells in vivo. Of significant importance, there were no obvious toxic effects of Fmev in the mice.

EXAMPLE 7

INHIBITION OF DNA SYNTHESIS BY Fmev

The present example demonstrates that Fmev exerts irreversible effects.

The ability of a single injection of Fmev to suppress tumor growth by >95% suggested that the effect of Fmev was irreversible. The inventors examined this possibility by measuring proliferation after incubating RasDC cells in vitro with Fmev, then washing the cells extensively to remove Fmev from the medium. Preincubation of RasDC cells with Fmev markedly inhibited their subsequent proliferation. The addition of either lovastatin, to prevent the accumulation of an inhibitor, or an exogenous source of IL-3 to provide an alternative signalling pathway, or both, was able to restore proliferation only partially.

The above data support the hypothesis that Fmev causes an irreversible inhibition of mevalonate metabolism. Previous studies examining the mechanism whereby Fmev inhibits sterol biosynthesis have demonstrated that the inhibitory activity of Fmev requires its phosphorylation by the enzymes catalyzing the phosphorylation of mevalonate (Nave et al. 1985). Once phosphorylated in the cell, Fmev is unable to exit the cell, and thereby continuously and irreversibly inhibits mevalonate metabolism.

EXAMPLE 8

INHIBITORY MEVALONATE PRODUCTS IN CELLS BLOCKED BY Fmev

The present inventors discovered that Fmev inhibits proliferation by causing the accumulation of an inhibitory product of mevalonate and that decreasing mevalonate synthesis with lovastatin then restored proliferation of the cells.

In cell fractionation studies that traced the fate of [3H] mevalonate in control and Fmev-blocked cells, Fmev was observed to completely block the incorporation of radiolabeled mevalonate into the lipid and protein fractions. In contrast, there was a marked increase in the incorporation of [$^3$H] mevalonate in the trichloracetic acid-soluble or aqueous fraction. Additional studies have demonstrated a similar distribution of radioactivity in cells fractionated by solubilization in chloroform:methanol:water with an increase in [$^3$H] mevalonate in the aqueous:methanol fraction.

Figure 9A:
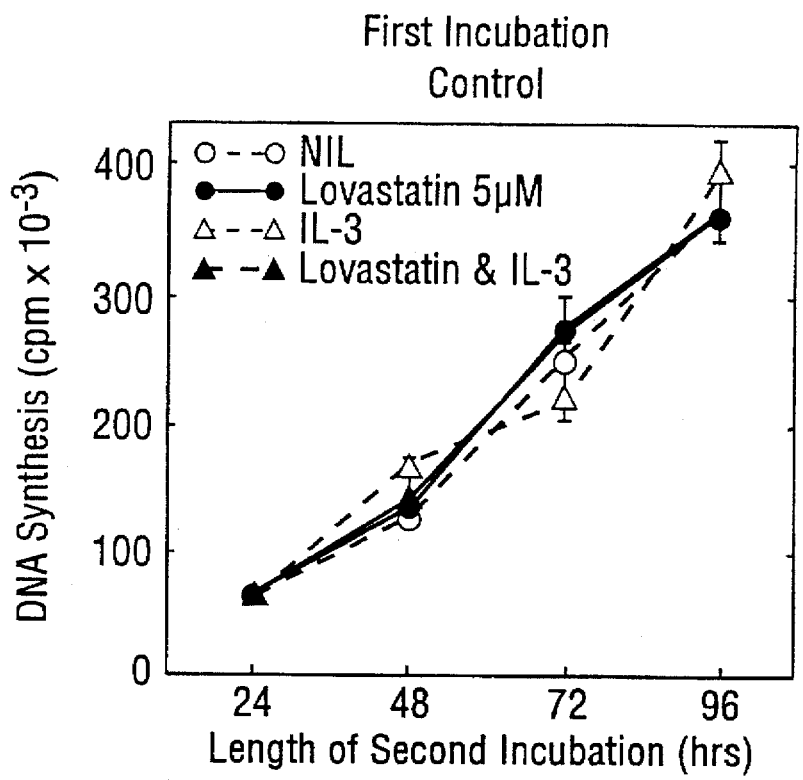
FIGS. 9A and 9B—Inhibition of DNA synthesis by initial incubation with Fmev. This figure contains two panels, FIG. 9A and FIG. 9B. RasDC cells were first incubated for 24 hours without (control) or with 500 μM Fmev. Cells were then washed extensively before incubating (5,000 cells/microtiter well) in complete medium with or without interleukin-3 (IL-3; source WEHI-3 conditioned medium) and with or without lovastatin 5 μM for an additional 24–96 hours (second incubation). RasDC cells DNA synthesis was quantitated at the end of each second incubation by the incorporation of [$^3$H] thymidine as described by Cuthbert & Lipsky (1991). Results are mean ±SEM of triplicate determinations.
Figure 9B:
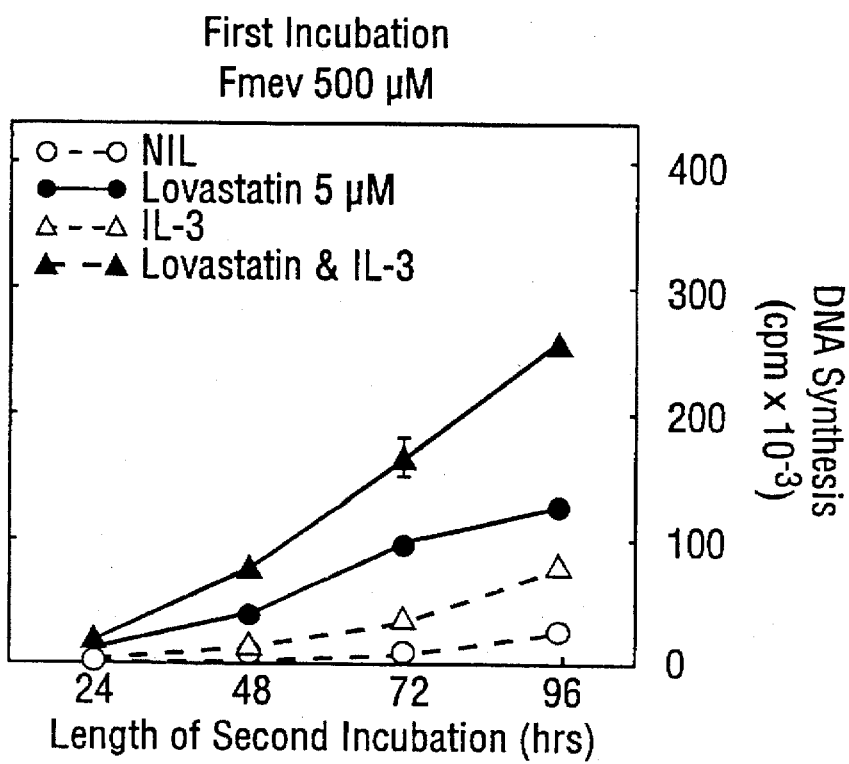
Figure 10:
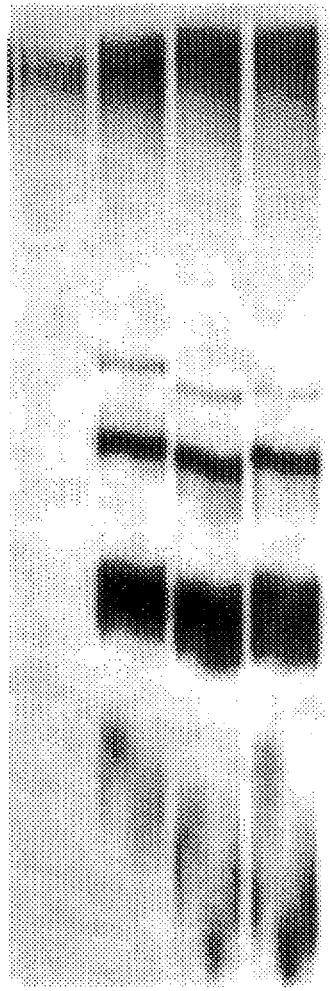
FIG. 10—Non-standard derivatives of mevalonate that may be responsible for selective inhibition of tumor growth. U-937 histiocytic lymphoma cells (ATCC CRL 1593) were incubated in complete medium (RPMI-1640 basal medium and 10% Iron-supplemented bovine calf serum) with [$^3$H] mevalonolactone (NEN) and with or without varying concentrations of Fmev as indicated. After 24 hours, cells were harvested, washed extensively to remove any unincorporated [$^3$H] mevalonate and then separated into chloroform-soluble (lipid), interphase or insoluble (protein) and aqueous; methanol-soluble ("aqueous") fractions as detailed (Cuthbert and Lipsky (1990)). The aqueous; methanol fraction was concentrated, resuspended and chromatographed using n-propanol: ammonium hydroxide: water (9:3;1) on channelled thin-layer chromatography plates. Standards and experimental compounds were visualized by fluorography. Authentic mevalonate ([$^3$H]-labeled; NEN), mevalonate-5-phosphate ([$^{14}$C]-labeled; Amersham) and mevalonate-5-pyrophosphate ([$^{14}$C]-labeled; Amersham) were used to identify the [$^3$H]-labeled mevalonolactone that had been converted to mevalonate-5-phosphate and mevalonate-5-pyrophosphate or remained unchanged as mevalonate. The two mevalonate-derived products not identified as mevalonate, mevalonate-5-phosphate or mevalonate-5-pyrophosphate do not co-migrate with authentic isopentenyl pyrophosphate, dimethylallyl pyrophosphate, geranyl pyrophosphate, farnesyl pyrophosphate or geranyl-geranyl pyrophosphate, all of which are down-stream products of normal mevalonate metabolism. These two undescribed products of mevalonate metabolism are only visualized in Fmev-blocked cells and are thus novel candidates for selective inhibitors of the proliferation of transformed cells.

The aqueous:methanol fraction, obtained from Fmev-blocked cells labeled with [$^3$H] mevalonate, has been separated by thin-layer chromatography using the solvent system n-propanol:ammonia hydroxide:water (6:3:1) and the compounds visualized by fluorography. In addition to the expected bands corresponding to the radiolabeled standards, mevalonate, mevalonate phosphate and mevalonate pyrophosphate, two additional bands were detected (FIGS. 9A and 9B). The migration characteristics of these bands differed from those of all mevalonate-derived products examined, including isopentenyl pyrophosphate, dimethylallyl pyrophosphate, geranyl pyrophosphate, farnesyl pyrophosphate and geranylgeranyl pyrophosphate. The compounds identified in these bands are potential candidate compounds for the mevalonate product essential for cell growth, the synthesis of which is not blocked by Fmev, as well as for the inhibitory product that accumulates in Fmev-blocked cells.

EXAMPLE 9

TREATMENT OF RAS-TRANSFORMED CANCER WITH FMEV

The present example provides a method that may be used to employ Fmev in the treatment of tumors, particularly oncogenic Ras cancers, in humans.

Patients for initial Phase I studies will generally be selected according to the following criteria. They will have:
 a) cancers with activated Ras;
 b) cancers that do not respond to chemotherapy and cannot be resected surgically; and
 c) tumor size or metastases size documented by computed tomography (CT)

Although the present invention is suitable for treating a very wide variety of ras-related tumors, patients for initial treatment would be likely to come from the following diagnostic categories:
 1. Non-small cell lung cancer diagnosed by biopsy and size quantitated by chest CT;
 2. Adenocarcinoma of the colon with hepatic metastases with primary tumor diagnosed by biopsy and hepatic metastases quantitated by abdominal CT;
 3. Pancreatic carcinoma with local extension or involvement of abdominal lymph nodes by CT.

The execution of cancer therapy is well-known to those practicing in this area. However, preferred treatment regimens are contemplated to be those that generally include the following steps:
 a) Intravenous infusion of 50 μmols Fmev in 1 liter of normal saline over 6 hours (estimated or desirable therapeutic concentration 10 μmols/liter);
 b) Hourly monitoring of routine vital signs during infusion and 4 hourly for following 48 hours;
 c) Daily measurement of kidney, liver, heart and lung function by biochemical tests and of bone marrow function by complete blood count for 7 days;
 d) Determination of tumor and/or metastases size by CT after 7 days and after 28 days for early (1 week) and later (1 month) responses;
 e) If no appreciable effect on size of tumor and/or metastases from initial dose then the following strategy would be employed:
  1. repeat infusion at same concentration but directly into artery supplying tumor and/or metastases;
  2. higher concentration infused intravenously until limited by toxicity, may be observed with 1 mmol/liter (no toxicity in T lymphocytes cultured in vitro for 4 days with 1 mM Fmev continuously present);
  3. longer infusion time (24 hours) or repeated 6 hour infusions daily for 5–7 days.

Following the demonstration of therapeutic efficacy with acceptable toxicity, then the effectiveness of the therapy on other tumors, and in conjunction with other therapies, would be determined.

EXAMPLE 10

PREPARATION OF MONO AND DI HALOGENATED MEVALONATE

The present example provides methods that may be used to prepare mono- and dihalogenated mevalonate for the practice of the claimed methods. The chemistry provided in Quistad and Cerf (1981 (Pr. Nauk. Inst. Chem. Org. Fiz. Politech. Wroclaw 22, 163)[28] was used to synthesize the mono fluromevalonate described in the present studies. The Quistad and Cerf article is specifically incorporated herein by reference for this purpose. This procedure employed the use of ethyl fluoroacetate in the preparation of 6-fluoromevalonate.

After synthesis, the halogenated mevalonate preparations were purified by chromatography by passing the preparation several times over a Silica gel. For use in the described methods, it is anticipated that the halogenated mevalonate preparation be at least partially purified. A partially purified preparation is defined for purposes of the present invention as an at least 80% pure preparation of the halogenated mevalonate as determined by capillary gas liquid chromatography (GLC). The halogenated mevalonate preparations of the invention are most preferably at least 98% pure as determined by GLC.

Most preferably, the preparation should be sequentially chromatographed over a Silica gel column at least three times in order to achive these levels of purity. Fmev preparations that were approximately between 98% pure and 99% pure by capillary GLC were obtained in this manner.

For the preparation of about 5.0 grams of the 6-Fmev, the following amounts of reagents were used:

| Aldrich | Catelog No. | | |
|---------|-------------|---|---|
| 16,381-3 | Ethyl fluoroacetate (98%) | 1 × 50.0 gm | 22.10 |
| 22575-4 | Allyl magnesium bromide (1.0 M in Ether) | 1 × 800.0 mL | 48.70 |
| 21346-4 | Sodium borohydride | 1 × 25.0 gm | 16.00 |
| 28,860-8 | Silica gel | 1 × 1.0 kgm | 76.00 |
| | Ethyl acetate | 1 × 4.0 L | |
| | Diethyl ether, ACS, Anhyd. | 1 × 4.0 L | |

Iodo, bromo, and chloro mevalonate derivatives may also be used in the practice of the claimed methods by, for example, the use of ethyl-iodoacetate, ethyl bromoacetate or ethyl cloroacetate in the Quistad protocol.

For use in the described methods, commercially available forms of mevalonate (such as, for example, from Sigma (mevalono-lactone) or as described in U.S. Pat. No. 3,119, 842), may be modified to include a halogen at any of the carbon sites on the mevalonate molecule, such as the 4-position or the 6-position of the molecule. Preferably, the halogen substitutions are to be made at the 6-position of the mevalonate molecule. These preferred embodiments of the halogenated mevalonate preparations may include the following compounds:

6-fluoro-mevalonate (6-Fmev)

6,6 di-fluoro-mevalonate (6,6-Fmev)

6-iodo-mevalonate (6-Imev)

6,6-di-iodomevalonate (6,6-Imev)

6-bromomevalonate (6-Brmev)

6,6-di-bromomevalonate (6,6-Brmev)

6-chloromevalonate (6-Clmev)

6,6-di-chloromevalonate (6,6-Clmev)

The chemistry provided in Reardon and Abeles (1987) (*Biochemistry*, 26:4717–4727), also describes a method that may be employed for preparing 6-fluorinated forms of mevalonate (6-Fmev and 6,6-Fmev). Materials to be used in the synthesis of the halogenated mevalonate preparations as described in the Reardon procedure may be purchased from Sigma Chemical Co. (Alkaline phosphatase, adenosine triphosphate, nicotinamide adenine dinucleotide (oxidized) nicotinamide adenine dinucleotide (reduced), triethylammonium bicarbonate, glucose 6-phosphate).

Crystalline orthophosphoric acid may be purchased from Fluka Chemical Co. Bis (triethyl-ammonium) phosphate may be prepared according to the method of Cornforth and Popjak (1969) (Methods Enzymol. 15,393), which reference is also specifically incorporated herein by reference for this purpose. Tris(tetrabutylammonium) pyrophosphate may be prepared according to the method of Davisson et al. (1985). Triethylammonium bicarbonate, TEAB, may be prepared by passing $CO_2$ gas, from dye ice, through a gas dispersion frit into a cold, stirred 1M solution of triethylamine until the pH is 7.5. The synthesis of isopentenyl pyrophosphate is described in Reardon & Abeles (1986)[37] Farnesyl pyrophosphate may be synthesized and purified by the procedure used for dimethylallyl pyrophosphate (Reardon & Abeles, 1986[37]) and further purified on XAD-2 resin (Cornforth & Popjak, 1969[38]). Mevalonate 5-phosphate may be synthesized by the published procedure (Foote & Wold, 1963[40]). The 6-substituted mevalonate preparations may be purified by flash chromatography on silica gel in ethyl acetate/ether, 2:1; the 6,6 forms purified by flash chromatography on silica gel in ethyl acetate/hexanes, 2:1; and any more highly halogenated forms, such as 6,6,6-Fmev may be purified by flash chromatography on silica gel in ether/hexanes, 2:1. The purity of halogenated mevalonate compounds may then be checked by $^1$H NMR, $^{13}$C NMR, and TLC.

To prepare the iodo-derivatives, iodine including reagents would be used in place of the fluorine containing reagents (e.g., ethyl bromodifluoroacetate). The modifications in the Quistad[29] or Reardon[30] procedure necessary to prepare the iodo-forms of mevalonate are expected to be within the ordinary skill of one in the biochemical and organochemical arts.

By way of example, the bromo-derivatives may be prepared by substituting an ethyl bromoacetate in the synthesis procedure of Quistad and Cerf (1981)[29]. Both the 6-Brmev and 6,6-Brmev may be prepared in this fashion.

By way of example the chloro-derivatives of mevalonate may be prepared by substituting a bromodichloroacetate for the bromodifluoroacetate in the Reardon and Abeles (1987)[30] procedure. Alternatively, ethyl chloroacetate may be employed in the Quistad protocol to provide chloro mevalonate preparations.

The following criterion may be used to screen and select particularly useful halogenated mevalonate forms for use in the described methods:

1. In vitro activity of the halogenated mevalonate to inhibit mevalonate metabolism in FDC-P1 cells and Ras DC (cell lines described in Boswell et al. (1990)[5] (See Example 2);
2. In vitro activity of the halogenated mevalonate to inhibit proliferation of FDC-P1 cells and Ras DC cells (See Example 4);
3. In vitro activity of the halogenated mevalonate to inhibit protein prenylation in H187 cells (cell line described in Miller et al.[24]) and H157 cells (cell line described in Mitsudomi et al. 1991[25]); and
4. In vivo activity of halogenated mevalonate to inhibit Ras DC cell tumor growth in DBA/2 mice (syngenic for Ras DC cells) injected with Ras DC cells. The halogenated mevalonate preparation will be injected either intra-peritoneally or intravenously at a concentration of about 10 μmoles (See Example 6); and tumor growth should be assessed after about 3 weeks. Halogenated mevalonate preparations that inhibit mevalonate metabolism, protein prenylation or cell proliferation in vitro or which inhibit Ras-dependent tumor growth, in vivo, will be useful in the practice of the claimed methods.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Almoguera et al., (1988) *Cell*, 53:549–554.
2. Barbacid, M., (1987) *Annu. Rev. Biochem.*, 56:779–827.
3. Beck et al., (1990) *J. Cell Biol.*, 110:1489–1499.
4. Bos, (1988) *Mut. Res.*, 195:255–271.
5. Boswell et al., (1990) *Exp. Hematol.*, 18:452–460.
6. Chesa et al., (1987) *Proc. Natl. Acad. Sci. U.S.A.*, 84:3234–3238.
7. Cuthbert and Lipsky, (1990) *J. Biol. Chem.*, 265:18568–18575.
8. Cuthbert and Lipsky, (1991) *J. Biol. Chem.*, 266:17966–17971.
9. DeClue et al., (1991) *Cancer Res.*, 51:712–717.
10. Downward et al., (1990) *Nature*, 346:719–723.
11. Faust and Kreiger, (1987) *J. Biol. Chem.*, 262:1996–2004.
12. Fearon and Vogelstein, (1990) *Cell*, 61:759–767.
13. Goldstein and Brown, (1990) *Nature*, 343:425–430.
14. Grand and Owen, (1991) *Biochem. J.*, 279:609–631.
15. Graves et al., (1992) *J. Immunol.*, 148:2417–2422.
16. Hancock et al., (1990) *Cell*, 63:133–139.
17. Hancock et al., (1989) *Cell*, 57:1167–1177.
18. Jackson et al., (1990) *Proc. Natl. Acad. Sci. U.S.A.*, 87:3042–3046.
19. Kaneko et al., (1978) *Eur. J. Biochem.*, 87: 313–321.
20. Lacy et al., (1991) *Science*, 254: 1782–1784.
21. Kato et al., (1992) *Proc. Natl. Acad. Sci. U.S.A.*, 89: 6403–6407.
22. Lu and Campisi, (1992) *Proc. Natl. Acad. Sci. U.S.A.*, 89:3889–3893.
23. Leonard et al., (1990) J. Biol. Chem., 265:5157–5160.
24. Miller et al., (1989) *J. Clin. Invest..*
25. Mitsudomi et al., (1991) *Oncogene* 6:1353–1362.
26. Mumby et al., (1990) *Proc. Natl. Acad. Sci. U.S.A.*, 87:5873–5877.
27. Nave et al., (1985) *Biochem. J.*, 227:247–254.
28. Niman et al., (1986) *Clin. Lab. Med.*, 6: 181–196.
29. Quistad and Cerf, (1981) Pt. Nauk. Inst. *Chem. Org. Fiz. Politech. Wroclaw*, 22:163–168.
30. Reardon and Abeles, (1987) Biochemistry, 26:4717–4722.

31. Reddy et al., (1982) *Nature*, 300:149–152.
32. Satoh et al., (1991) *Proc. Natl. Acad. Sci. U.S.A.*, 88:3314–3318.
33. Skorski et al., (1992) *J. Exp. Med.*, 175:743–750.
34. Sullivan et al., (1991) *Science*, 252:718–721.
35. Willumsen et al., (1984) *EMBO J.*, 3:2581–2585.
36. Davisson et al., (1985) *Methods Enzymol.*, 110:130.
37. Reardon and Abeles, (1986) *Biochemistry*, 25:5609.
38. Cornforth and Popjak, *Methods Enzymol.*, 15:359.
39. Popjack, G., (1969) *Methods Enzymol.*, 15:393.
40. Foote and Wold, (1963) *Biochemistry*, 2:1254.

What is claimed is:

1. A method for inhibiting proliferation of Ras-transformed cells sensitive to fluoromevalonate comprising:

contacting cells that include Ras-transformed cells with an effective amount of fluoro mevalonate; and inhibiting proliferation of the Ras-transformed cells wherein cytoplasmic Ras of Ras-transformed cells is depleted and proliferation of Ras-transformed cells is selectively inhibited.

2. The method of claim 1 wherein the fluoro mevalonate is 6-fluoromevalonate.

3. The method of claim 1 wherein the Ras transformed cells are Ras-transformed lung cells, colon cells, breast cells, urinary tract cells, stomach cells, liver cells, cervical cells, ovarian cells, pancreas cells, gall bladder cells, fibrosarcoma cells, rhabdomyosarcoma cells, bone marrow cells or teratocarcinoma cells.

4. The method of claim 1 wherein the Ras transformed cells are RasDC cells.

5. The method of claim 1 wherein the Ras transformed cells are bone marrow cells.

6. The method of claim 1 wherein the Ras transformed cells are lymphoma cells.

7. The method of claim 1 wherein the Ras transformed cells are human bladder cells.

8. The method of claim 1 wherein the Ras transformed cells are cells having a mutated $H^-$, $K^-$ or $N^-$ ras gene.

9. A method for inhibiting proliferation of Ras-transformed cells sensitive to treatment with fluoromevalonate in an animal comprising:

administering a therapeutically effective amount of fluoromevalonate in a pharmaceutically acceptable carrier to said animal; and inhibiting proliferation of the Ras-transformed cells wherein cytoplasmic Ras of Ras-transformed cells is depleted and proliferation of Ras-transformed cells is selectively inhibited.

10. The method of claim 1 or 9 wherein the Ras-transformed cells are Ras-transformed human cells.

11. The method of claim 9 wherein the fluoro mevalonate is 6-fluoromevalonate.

12. The method of claim 9 wherein the Ras transformed cells are Ras transformed lung, breast, urinary tract, stomach, colon, liver, cervical, ovarian, pancreatic, or gall bladder cells.

13. The method of claim 11 wherein the therapeutically effective amount of fluoromevalonate is between about 1 mg/kg and about 50 mg/kg of 6-fluoromevalonate.

14. The method of claim 11 wherein the therapeutically effective amount of fluoromevalonate is about 10 mg/kg of 6-fluoromevalonate.

15. The method of claim 9 wherein the Ras-transformed cells are further described as a tumor.

16. The method of claim 9 wherein the Ras transformed cells are in an animal having adenocarcinoma, leukemia, fibrocarcinoma, AML, CML, ALL, Burkitt's lymphoma or Hodgkins disease.

* * * * *